(12) United States Patent  
Yamada

(10) Patent No.: US 11,963,794 B2  
(45) Date of Patent: Apr. 23, 2024

(54) PROBE HOLDER

(71) Applicant: NATIONAL INSTITUTE OF ADVANCED INDUSTRIAL SCIENCE AND TECHNOLOGY, Tokyo (JP)

(72) Inventor: Toru Yamada, Ibaraki (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 692 days.

(21) Appl. No.: 17/256,412

(22) PCT Filed: Dec. 20, 2019

(86) PCT No.: PCT/JP2019/050042  
§ 371 (c)(1),  
(2) Date: Dec. 28, 2020

(87) PCT Pub. No.: WO2020/183854  
PCT Pub. Date: Sep. 17, 2020

(65) Prior Publication Data  
US 2021/0219916 A1 Jul. 22, 2021

(30) Foreign Application Priority Data  
Mar. 13, 2019 (JP) ................. 2019-046279

(51) Int. Cl.  
*A61B 5/00* (2006.01)
(52) U.S. Cl.  
CPC .......... *A61B 5/6835* (2013.01); *A61B 5/0082* (2013.01); *A61B 5/6814* (2013.01)
(58) Field of Classification Search  
CPC ... A61B 5/6835; A61B 5/0082; A61B 5/6814; A61B 10/00  
See application file for complete search history.

(56) References Cited

U.S. PATENT DOCUMENTS 7,039,454 B1 * 5/2006 Kaga ................. G01N 21/4795  
374/161  
10,307,062 B2 * 6/2019 Inoue ................... A61B 5/6814  
(Continued)

FOREIGN PATENT DOCUMENTS

JP 2002-291751 A 10/2002  
JP 2009-178192 A 8/2009  
(Continued)

OTHER PUBLICATIONS

Yamada, T., et al., "Functional near-infrared spectroscopy for monitoring macaque cerebral motor activity during voluntary movements without head fixation", Scientific Reports, Aug. 9, 2018, vol. 8, 11941, pp. 1-12.

(Continued)

*Primary Examiner* — Joel Lamprecht  
(74) *Attorney, Agent, or Firm* — Hoffmann & Baron, LLP

(57) ABSTRACT

The problem is to provide a probe holder for fixing, using a simple configuration, a plurality of probes in a state in which the positional relationships of the probes are defined. To solve the problem, provided is a probe holder for holding probes for emitting or detecting light and attaching the probes to the head of a subject, the probe holder including: a plurality of basic units each holding three of the probes with a single plate; and a plurality of couplers each linking a respective one of the three of the probes and adjacent probes to form a plurality of adjacent probes that are linked at a point equidistant from the plurality of adjacent probes, each probe in the plurality of adjacent probes being included in a different one of the plurality of basic units.

11 Claims, 9 Drawing Sheets

(56) References Cited

U.S. PATENT DOCUMENTS

| | | | |
|---|---|---|---|
| 2004/0054271 A1 | 3/2004 | Maki et al. | |
| 2009/0209837 A1* | 8/2009 | Hirabayashi | A61B 5/14553 600/344 |
| 2013/0066214 A1 | 3/2013 | Inoue et al. | |
| 2017/0311857 A1 | 11/2017 | Bae et al. | |
| 2017/0319072 A1 | 11/2017 | Bae et al. | |

FOREIGN PATENT DOCUMENTS

| | | |
|---|---|---|
| JP | 2015-100410 A | 6/2015 |
| JP | 2017-35174 A | 2/2017 |
| WO | WO 2011/114479 A1 | 9/2011 |

OTHER PUBLICATIONS

Kawaguchi, H., et al., "Functional near infrared spectroscopy for awake monkey to accelerate neurorehabilitation study", Proceedings of SPIE, Feb. 8, 2017, vol. 10051, pp. 1-8.

* cited by examiner

PROBE HOLDER

CROSS-REFERENCE TO RELATED APPLICATIONS

The present application is the U.S. National Phase of PCT/JP2019/050042, filed on Dec. 20, 2019, which claims priority to Japanese Patent Application No. 2019-046279, filed on Mar. 13, 2019, the entire contents of which are incorporated herein by reference.

BACKGROUND

Technical Field

The present invention relates to techniques for holding probes for measuring brain functions.

Related Art

As a technique for measuring the functions of a brain, functional near-infrared spectroscopy (fNIRS) has been known. This technique conventionally involves installing probes for optical emission and luminance detection on the head surface of a subject.

Patent Literature 1 discloses a probe holder having high rigidity and capable of holding the probes vertically and intimately onto curved surfaces of the head of various subjects, and maintaining the arrangement. Patent Literature 2 discloses a biological information acquiring device with which it is possible to cause electrode portions and light-receiving portions to be properly, highly densely, and intimately attached to a wide area on the surface of a specific location subject to individual differences depending on the subject and having a complicated curved surface shape.

CITATION LIST

Patent Literature

Patent Literature 1: JP 2009-178192 A
Patent Literature 2: JP 2017-035174 A

SUMMARY

Technical Problem

The probe holder described in Patent Literature 1, as illustrated in FIG. 4 thereof, has a structure that requires as many fasteners 8 as there are the probes. Accordingly, a large number of screws are required when multichannel fNIRS measurement is performed.

Further, the biological information acquiring device described in Patent Literature 2 has a structure such that, as described in paragraph of the document and as illustrated in FIG. 3 and FIG. 5 thereof, for example, measuring sub-units 1 are connected by links 17 formed from a freely curving flexible substrate. Accordingly, there is the problem that accurate positional adjustment cannot be made between the light-receiving portions and the like included in different measuring sub-units 1.

The present invention was made to solve the problem, and aims to provide a probe holder for fixing, using a simple configuration, a plurality of probes in a state in which the positional relationships of the probes are defined.

Solution to Problem

In order to solve the problem, the present invention provides a probe holder for holding probes for emitting or detecting light and attaching the probes to the head of a subject, the probe holder including: a plurality of basic units each holding three of the probes with a single plate; and a plurality of couplers each linking a respective one of the three of the probes and adjacent probes to form a plurality of adjacent probes that are linked at a point equidistant from the plurality of the adjacent probes, each probe in the plurality of adjacent probes being included in a different one of the plurality of basic units.

Advantageous Effects of Invention

According to the present invention, it is possible to provide a probe holder for fixing, using a simple configuration, a plurality of probes in a state in which the positional relationships of the probes are defined.

BRIEF DESCRIPTION OF THE DRAWINGS

FIG. 3 is a cross sectional view illustrating a structure of a basic unit 2a configured of a planar plate 3a.

DETAILED DESCRIPTION

Figure 1:
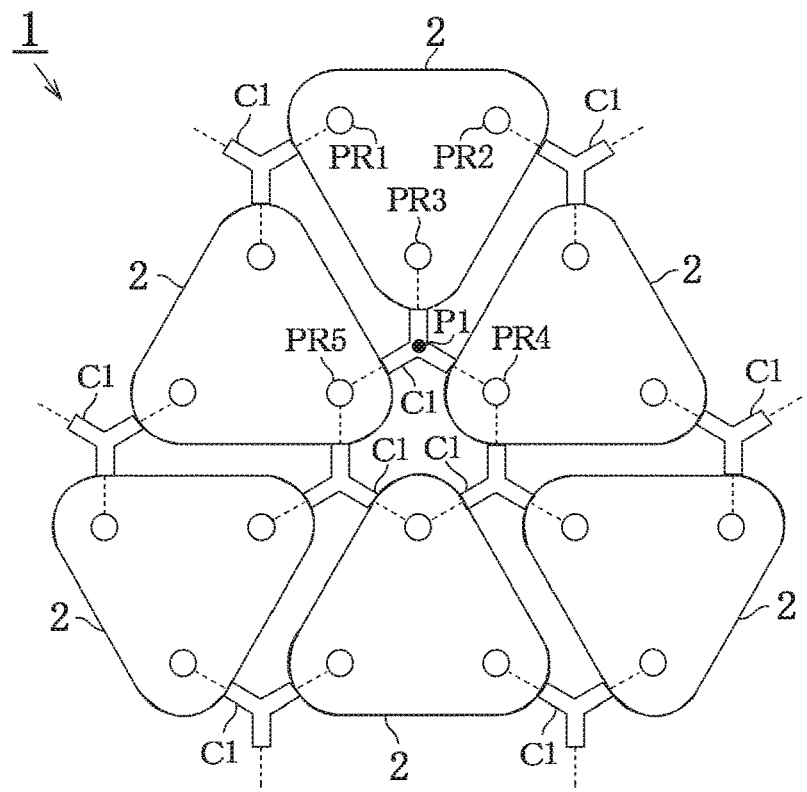
FIG. 1 is a plan view illustrating a configuration of a probe holder 1 according to a first embodiment of the present invention.

In the following, embodiments of the present invention will be described with reference to the drawings. In the drawings, similar reference signs designate similar or equivalent portions.

FIRST EMBODIMENT

FIG. 1 is a plan view illustrating a configuration of a probe holder 1 according to a first embodiment of the present invention. As illustrated in FIG. 1, the probe holder 1 according to the first embodiment of the present invention holds and attaches probes for fNIRS measurement to the head of a subject, the probes being disposed at lattice points over a triangular lattice and emitting or detecting light. The probe holder 1 is provided with: a plurality of basic units 2 each holding, with a single plate, three probes PR1 to PR3 which are disposed at the vertexes of a regular triangle and are thereby disposed adjacent to each other; and couplers each linking a plurality of adjacent probes respectively included in different basic units 2, at a central point that is equidistant from the plurality of probes.

Thus, the basic unit 2, by holding the three probes PR1 to PR3, can form a three-point support structure having the probes as legs, making it possible to obtain a local stability on the head surface of the subject. By linking and integrating a plurality of the basic units 2 having such structure, it is possible to attach a multichannel probe group as a whole to any curved surface the head surface may have in a stable manner.

Although FIG. 1 illustrates six basic units 2, the number of the basic units 2 that are linked as illustrated in FIG. 1 may be an arbitrary natural number, whereby multichannel arrangements of probes having various sizes and shapes as a whole can be realized.

Meanwhile, the couplers linking a plurality of basic units 2 by the method described above serve the role of linking adjacent basic units 2 to each other at a certain distance and an appropriate angle.

In the probe holder 1 illustrated in FIG. 1, the coupler C1, for example, links three adjacent probes PR3 to PR5, which are respectively included in three different basic units 2, to each other at a central point P1 that is equidistant from the three probes PR3 to PR5, whereby the three adjacent basic units 2 are linked with each other. In this way, the mutual distances between the probes PR3 to PR5 are maintained to be approximately equal to the mutual distances between the probes PR1 to PR3 of the basic unit 2.

Figure 2:
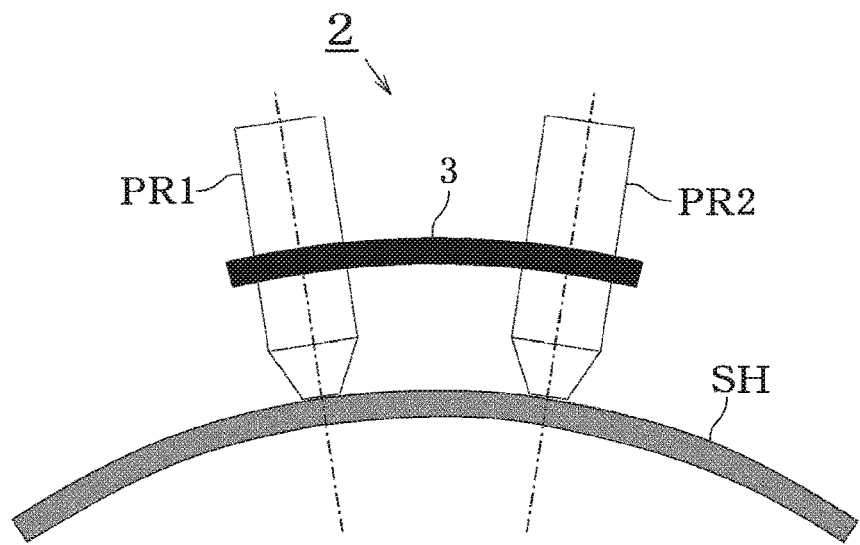
FIG. 2 is a cross sectional view illustrating a structure of basic units 2 illustrated in FIG. 1.

FIG. 2 is a cross sectional view illustrating a structure of the basic units 2 illustrated in FIG. 1. As illustrated in FIG. 2, the basic unit 2 includes a single rigid plate 3 having a predetermined curvature and holding the three probes PR1 to PR3. In the figure (as in other figures), the dashed and single-dotted lines indicate the central axes of the probes PR1, PR2, which have a substantially cylindrical shape, where the curvature of the rigid plate 3 is determined such that the central axes are in a direction normal to the head surface SH. The predetermined curvature is preferably an average curvature of the head surface SH of the subject, for example.

FIG. 2 illustrates a cross section of the basic unit 2 when the probes PR1, PR2 are viewed from the probe PR3 in FIG. 1. In FIG. 2, the cross section of the probe PR3 is omitted.

Figure 3:
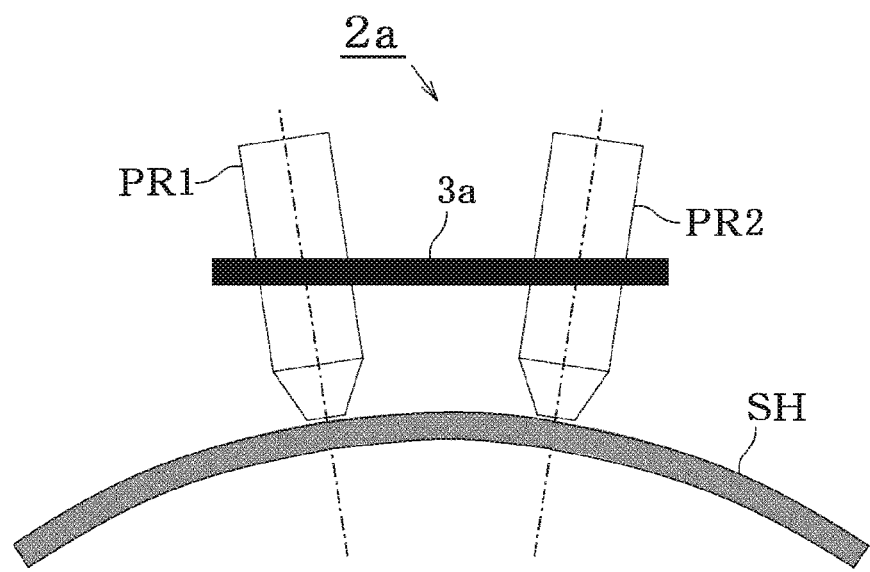

Instead of the rigid plate 3 with a predetermined curvature, a planar plate may be used. In this case, as illustrated in FIG. 3, the probes PR1 to PR3 are mounted to a planar plate 3*a* at an appropriate inclination angle so that the central axes of the probes indicated by the dashed and single-dotted lines are aligned as much as possible with a direction normal to the head surface SH. In the following, examples of the coupler C1 will be described.

EXAMPLE 1

Figure 4:
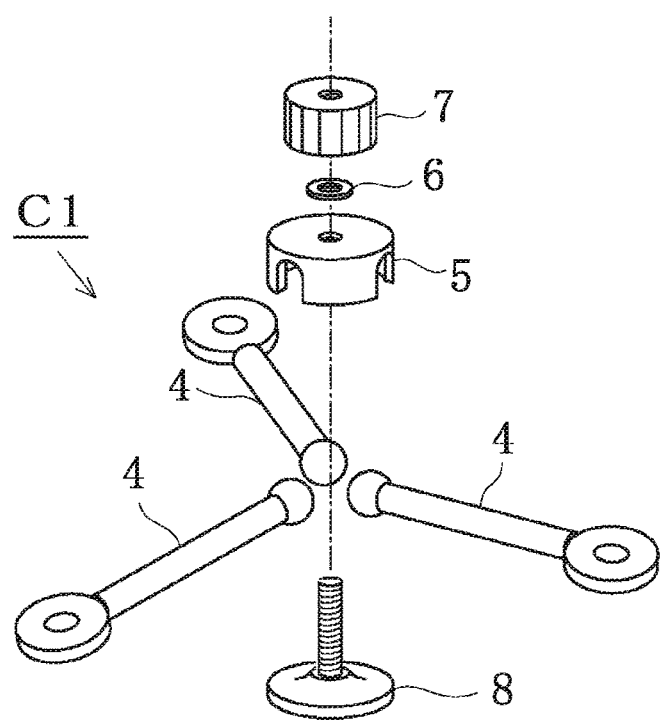
FIG. 4 is a perspective view illustrating Example 1 of couplers C1 illustrated in FIG. 1.

FIG. 4 is a perspective view illustrating Example 1 of the couplers C1 illustrated in FIG. 1. As illustrated in FIG. 4, the coupler C1 includes: three arms 4 each having a spherical end; a cap part 5 accommodating the spherical ends and having slits which are formed at 120-degree intervals around the central axis and have the same width as the width of the arms 4, the slits having the three arms 4 fitted therein; an O-ring 6 lying directly on the cap part 5; and a female screw 7 and a male screw 8 by which the arms 4 and the cap part 5 are fastened together vertically with the O-ring 6 therebetween. The structure allows each of three arms 4 to be movable vertically in a central axis direction indicated by the dashed and single-dotted line. Additionally, the three arms 4 are formed of a material enabling twisting of each of the arms around the axis thereof.

With the coupler C1 having the structure described above, because the height of the slits corresponds to a range of motion of the arms 4, it is possible to adjust the angle (lateral angle) of the arms 4 as viewed laterally, while maintaining a constant angle (in-plane angle) between the three arms 4 as viewed from above. That is, by tightening the female screw 7 and the male screw 8 after the probe holder 1 is attached to the head of the subject, the group of probes can be fixed to the head of the subject while maintaining the mutual in-plane angle and with the lateral angle adjusted appropriately.

Figure 5:
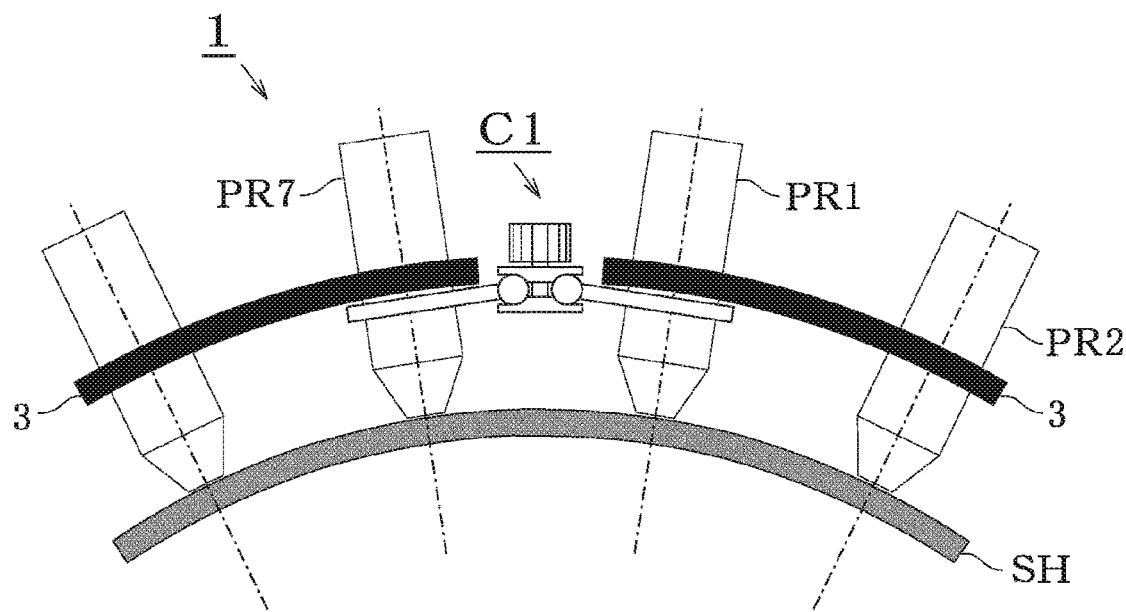
FIG. 5 is a cross sectional view illustrating a structure of the probe holder 1 where the basic units 2 illustrated in FIG. 2 adjacent to each other are coupled by the coupler C1 illustrated in FIG. 4.
Figure 6:
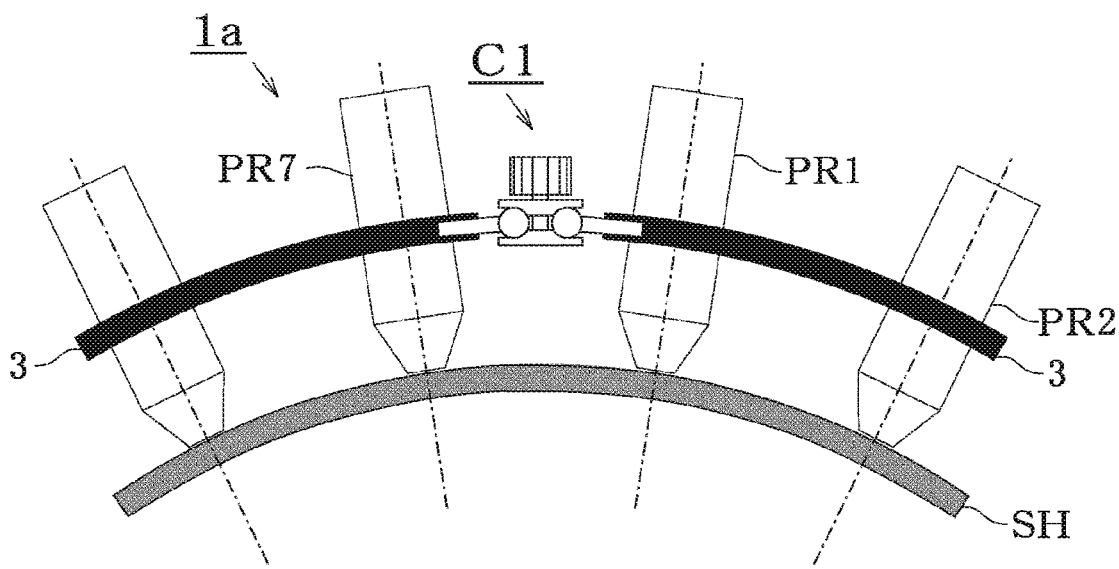
FIG. 6 is a cross sectional view illustrating a structure of a probe holder 1a where rigid plates 3 illustrated in FIG. 2 adjacent to each other are coupled by the coupler C1 illustrated in FIG. 4.
Figure 7:
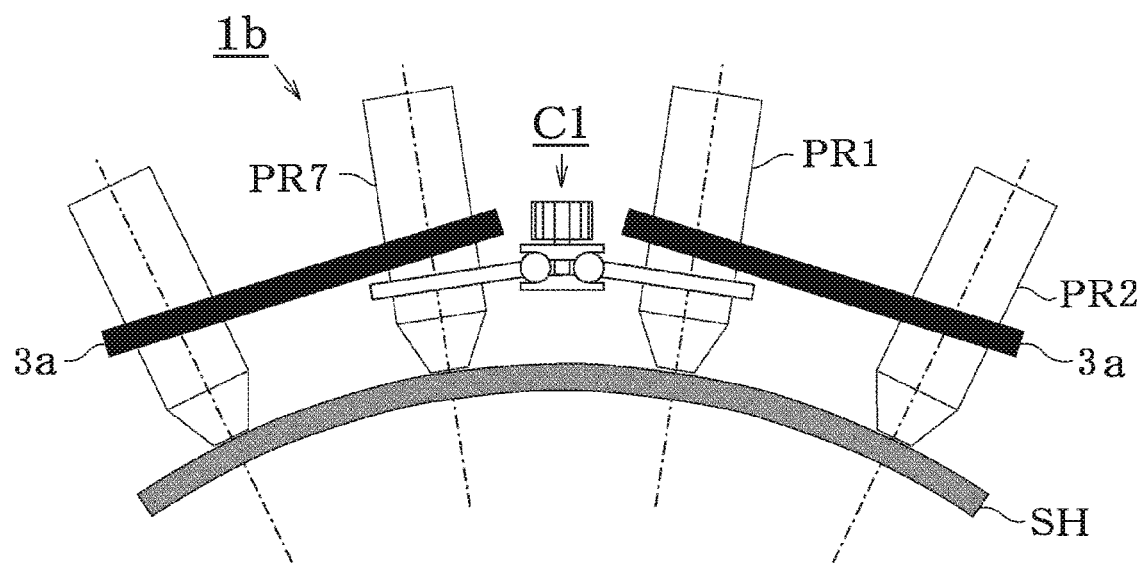
FIG. 7 is a cross sectional view illustrating a structure of a probe holder 1b where the basic units 2a illustrated in FIG. 3 adjacent to each other are coupled by the coupler C1 illustrated in FIG. 4.
Figure 8:
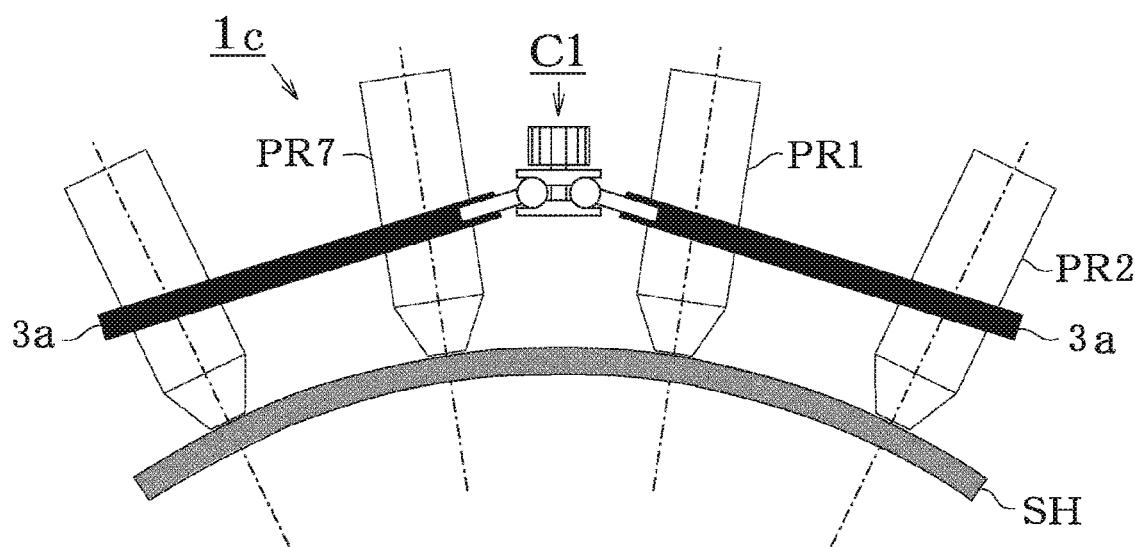
FIG. 8 is a cross sectional view illustrating a structure of a probe holder 1c where the planar plates 3a illustrated in FIG. 3 adjacent to each other are coupled by the coupler C1 illustrated in FIG. 4.

The coupler C1 illustrated in FIG. 4 has the arms 4 joined to probes PR1, PR7 as illustrated in FIG. 5, or joined to the rigid plate 3, as illustrated in FIG. 6. Needless to say, it is also possible, as illustrated in FIG. 7 and FIG. 8, for the coupler C1 of FIG. 4 to couple the basic units 2*a* configured of the planar plate 3*a* illustrated in FIG. 3, instead of the rigid plate 3 illustrated in FIG. 2.

EXAMPLE 2

Figure 9:
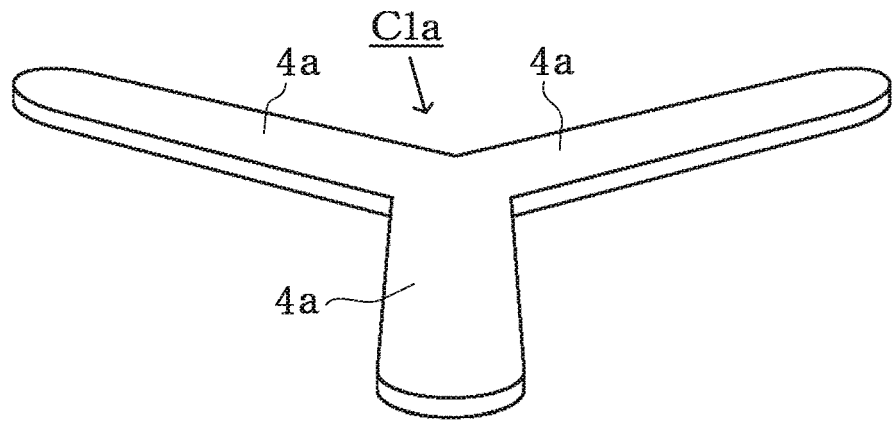
FIG. 9 is a perspective view illustrating Example 2 of the couplers C1 illustrated in FIG. 1.

FIG. 9 is a perspective view illustrating Example 2 of the couplers C1 illustrated in FIG. 1. As illustrated in FIG. 9, the coupler C1*a* of the present example is a three-pronged plate-like structure which has three arms 4*a* at the intervals with the in-plane angle of 120 degrees, and which is integrally formed from thermoplastic resin. The in-plane angle and the number of the arms 4*a* may have various values depending on the number of the probes coupled by the coupler C1.

As the thermoplastic resin, it is possible to use a resin described in JP 2006-131716 A that deforms when heated to about 40° C. and can be rapidly cured by cooling to ordinary temperature.

With the coupler C1*a* of the present example, when the subject wears the probe holder, the resin can be softened by the body heat or the heat of a drier and the like so that the curvature of the arms 4*a* can be adjusted in accordance with the shape of the head of the subject, and then the resin can be cooled to room temperature and cured. In this way, it is possible to attach the probe holder in a stable manner while maintaining a constant in-plane angle between the probes joined to the arms 4a.

Figure 10:
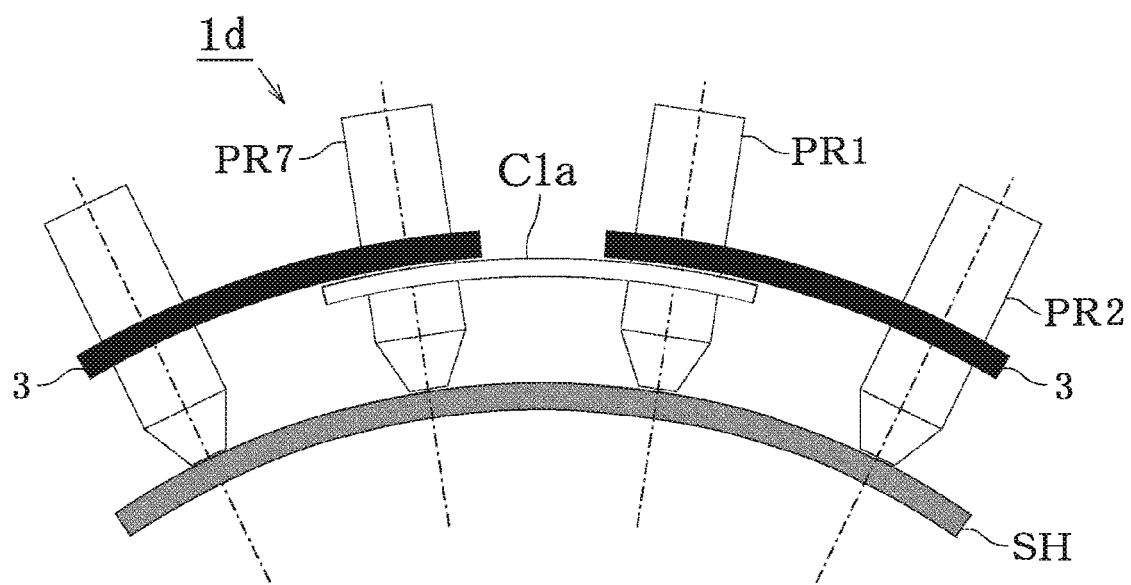
FIG. 10 is a cross sectional view illustrating a structure of a probe holder 1d where the basic units 2 illustrated in FIG. 2 adjacent to each other are coupled by a coupler C1a illustrated in FIG. 9.
Figure 11:
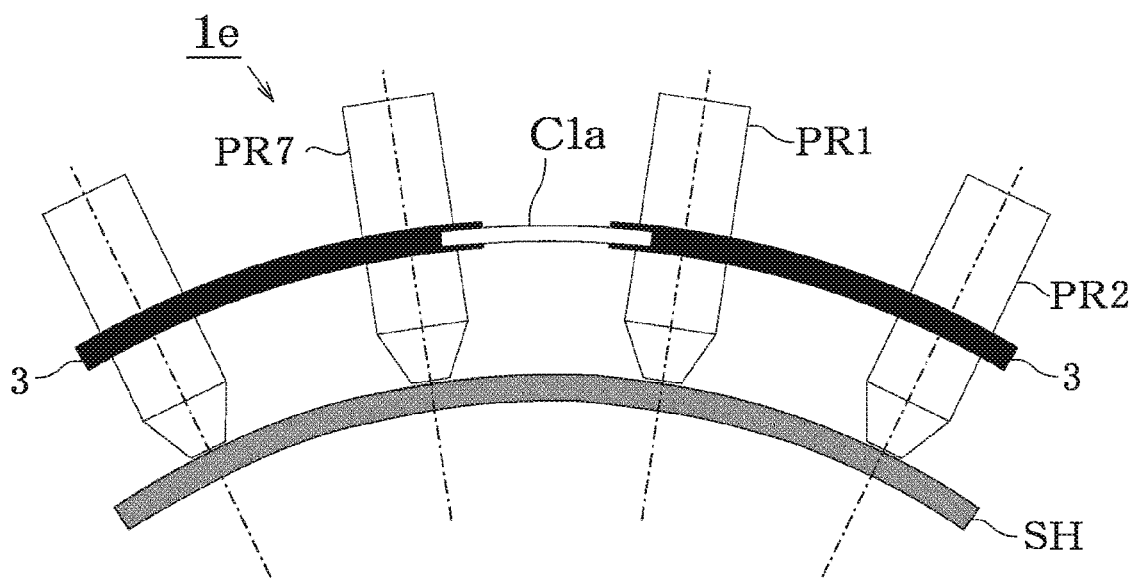
FIG. 11 is a cross sectional view illustrating a structure of a probe holder 1e where the rigid plates 3 illustrated in FIG. 2 adjacent to each other are coupled by the coupler C1a illustrated in FIG. 9.
Figure 12:
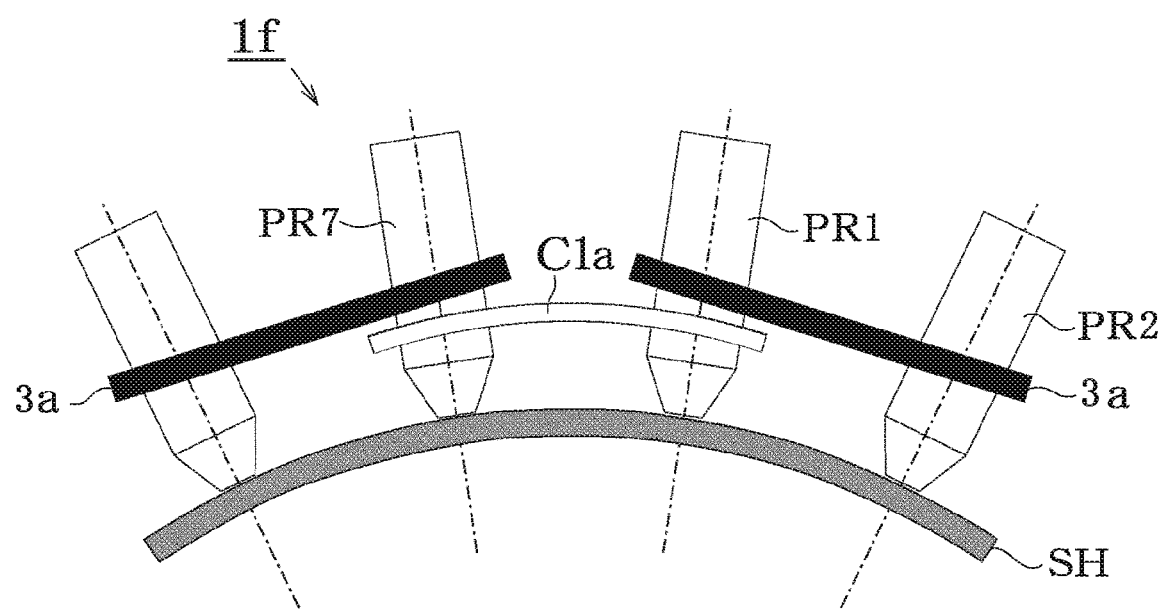
FIG. 12 is a cross sectional view illustrating a structure of a probe holder 1f where the basic units 2a illustrated in FIG. 3 adjacent to each other are coupled by the coupler C1a illustrated in FIG. 9.
Figure 13:
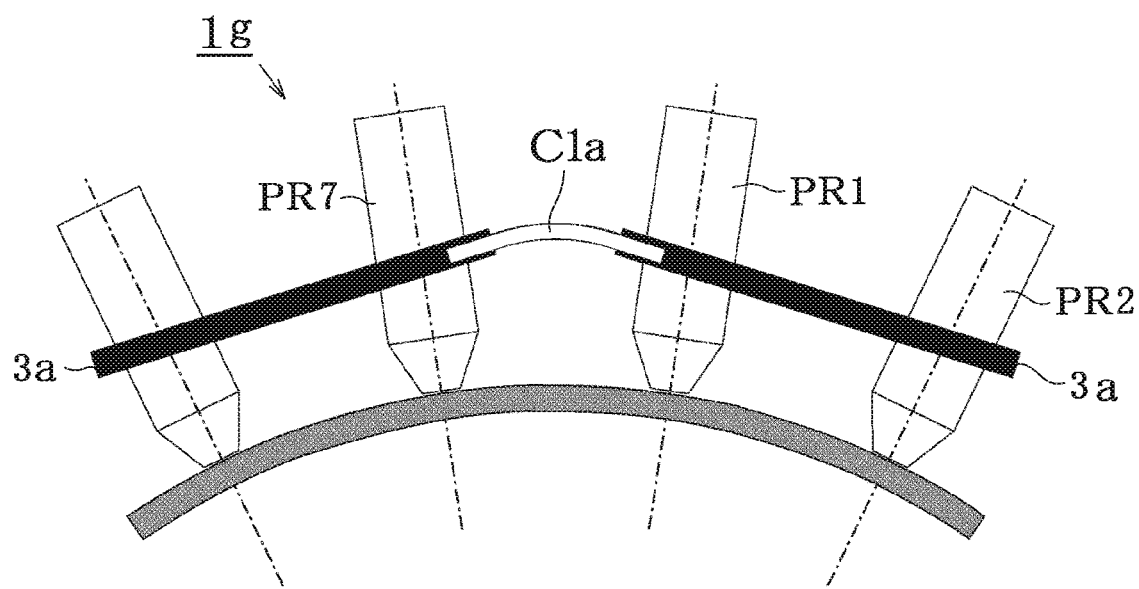
FIG. 13 is a cross sectional view illustrating a structure of a probe holder 1g where the planar plates 3a illustrated in FIG. 3 adjacent to each other are coupled by the coupler C1a illustrated in FIG. 9.

The coupler C1a has the arms 4a joined to the probes PR1, PR7 as illustrated in FIG. 10, or joined to the rigid plate 3, as illustrated in FIG. 11. Needless to say, it is also possible, as illustrated in FIG. 12 and FIG. 13, for the coupler C1a illustrated in FIG. 9 to couple the basic units 2a configured of the planar plate 3a illustrated in FIG. 3, instead of the rigid plate 3 illustrated in FIG. 2.

EXAMPLE 3

Figure 14:
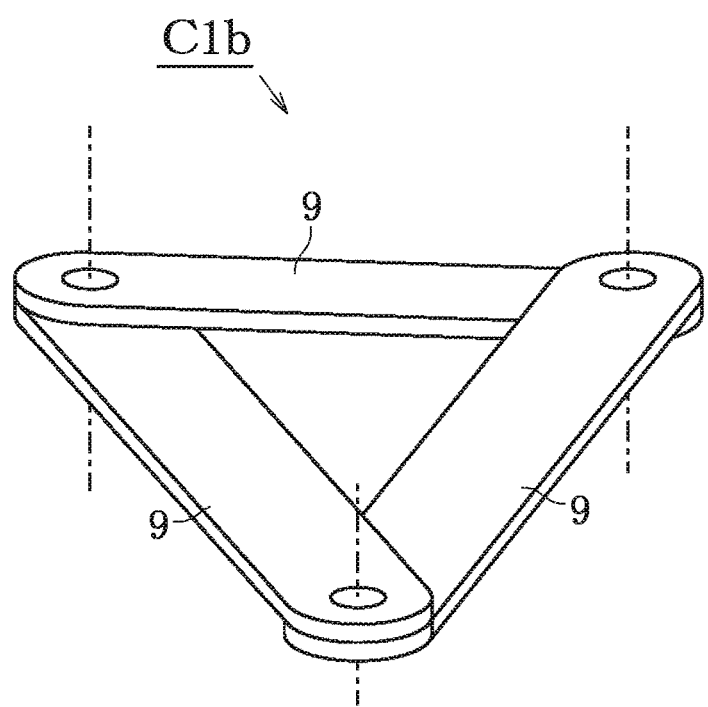
FIG. 14 is a perspective view illustrating Example 3 of the couplers C1 illustrated in FIG. 1.

FIG. 14 is a perspective view illustrating Example 3 of the couplers C1 illustrated in FIG. 1. As illustrated in FIG. 14, a coupler C1b of the present example has a structure in which I-shaped plate-like structures 9 made of the thermoplastic resin are joined together in a regular triangle shape.

In the coupler C1b, the plate-like structures 9 are joined together in a freely rotatable state with respect to probe central axes indicated by the dashed and single-dotted lines, so that, when bent along the head of the subject, the internal angles of the triangle formed by the three plate-like structures 9 can be increased.

With the coupler C1b of the present example, it is possible to maintain a constant distance between the probes no matter what the curved surface of the head surface of the subject is like.

As described above, the probe holder 1 according to the first embodiment of the present invention is configured such that a plurality of basic units 2 can be linked and fixed by the coupler C1 defining mutual angles and distances. Accordingly, it is possible, using a simple configuration, to adjust the arrangement of the probes PR1 to PR5 and to integrally increase the rigidity of the probes PR1 to PR5 and the probe holder 1, while ensuring a certain strictness with respect to any curved surface that the head of the subject may have. In this way, it is possible to achieve highly stable holding of the probes PR1 to PR5 on the head of the subject.

SECOND EMBODIMENT

Figure 15:
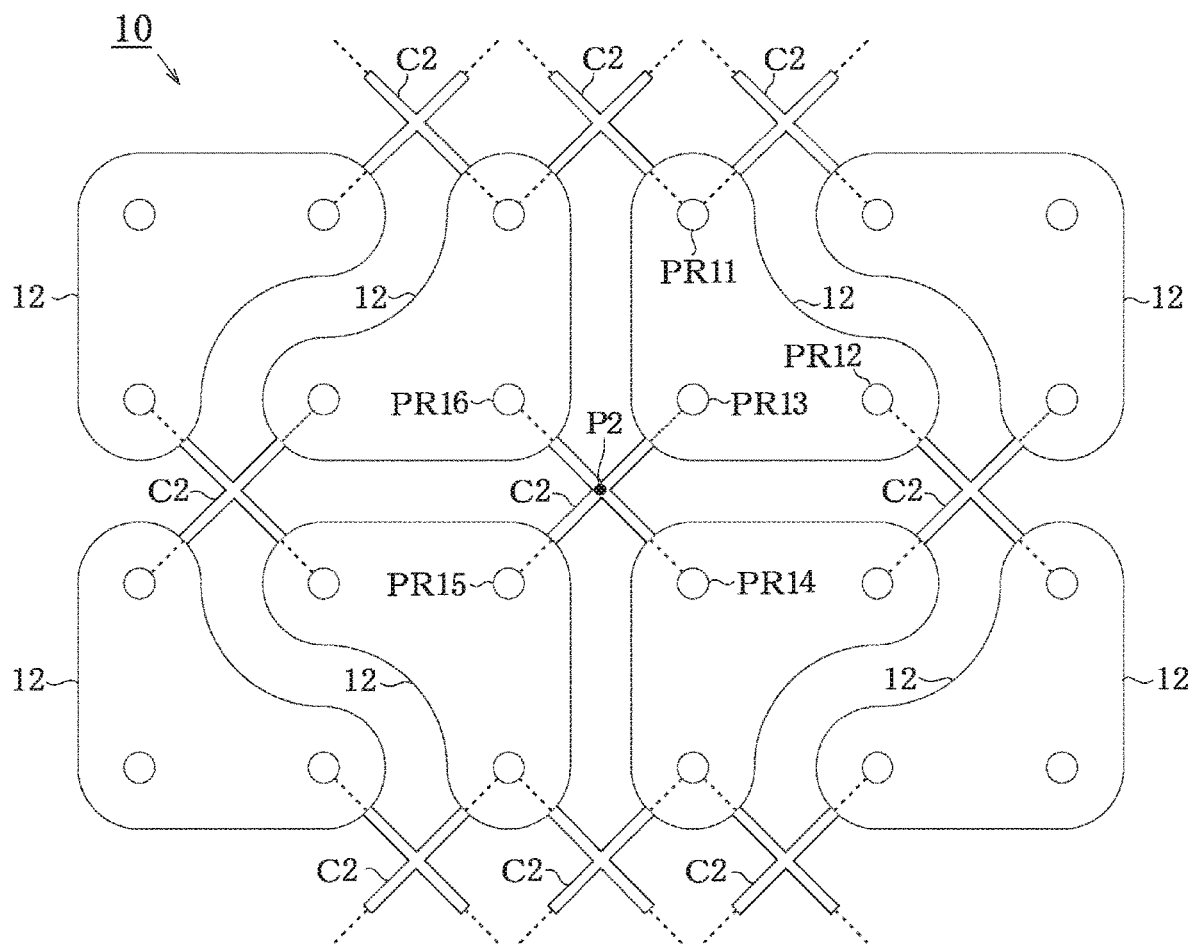
FIG. 15 is a plan view illustrating a configuration of a probe holder 10 according to a second embodiment of the present invention.

FIG. 15 is a plan view illustrating a configuration of the probe holder 10 according to a second embodiment of the present invention. As illustrated in FIG. 15, the probe holder 10 according to the second embodiment of the present invention holds and attaches probes for fNIRS measurement to the head of a subject, the probes being disposed at lattice points over a square lattice and emitting or detecting light. The probe holder is provided with: a plurality of basic units 12 each holding, with a single plate, three probes PR11 to PR13 which are disposed at the vertexes of an isosceles right triangle, for example, and are thereby disposed adjacent to each other; and couplers C2 which link a plurality of adjacent probes PR13 to PR16, which are respectively included in different basic units 12, for example, to each other at a central point P2 that is equidistant from the plurality of probes PR13 to PR16.

Thus, the basic unit 12, by holding the three probes, can form a three-point support structure having the probes as legs, making it possible to obtain a local stability on the head surface of the subject. By linking and integrating a plurality of the basic units 12 having such structure, it is possible to attach a multichannel probe group as a whole to any curved surface the head surface may have in a stable manner.

Although FIG. 15 illustrates eight basic units 12, the number of the basic units 12 linked as illustrated in FIG. 15 may be an arbitrary natural number, whereby multichannel arrangements of probes having various sizes and shapes as a whole can be realized.

Meanwhile, the couplers linking a plurality of basic units 12 by the method described above serve the role of linking adjacent basic units 12 to each other at a certain distance and an appropriate angle.

In the probe holder 10 illustrated in FIG. 15, the coupler C2 links the four adjacent basic units 12 to each other by linking the four adjacent probes PR13 to PR16 respectively included in the four different basic units 12 at the central point P2 that is equidistant from the four probes PR13 to PR16.

For the couplers C2 illustrated in FIG. 15, examples similar to Examples 1 to 3 of the first embodiment described above may be adopted. That is, in correspondence to Example 1, a coupler obtained by increasing the number of the arms 4 of the coupler C1 illustrated in FIG. 4 to four may be used, whereby operational effects similar to those of Example 1 can be obtained. In this case, the slits of the cap part 5 are formed at 90-degree in-plane intervals.

Further, in correspondence to Example 2, a coupler obtained by increasing the number of the arms 4a of the coupler C1a illustrated in FIG. 9 to four may be used, whereby operational effects similar to those of Example 2 can be obtained. In this case, the four arms 4a are formed at the intervals with the in-plane angle of 90 degrees.

Figure 16:
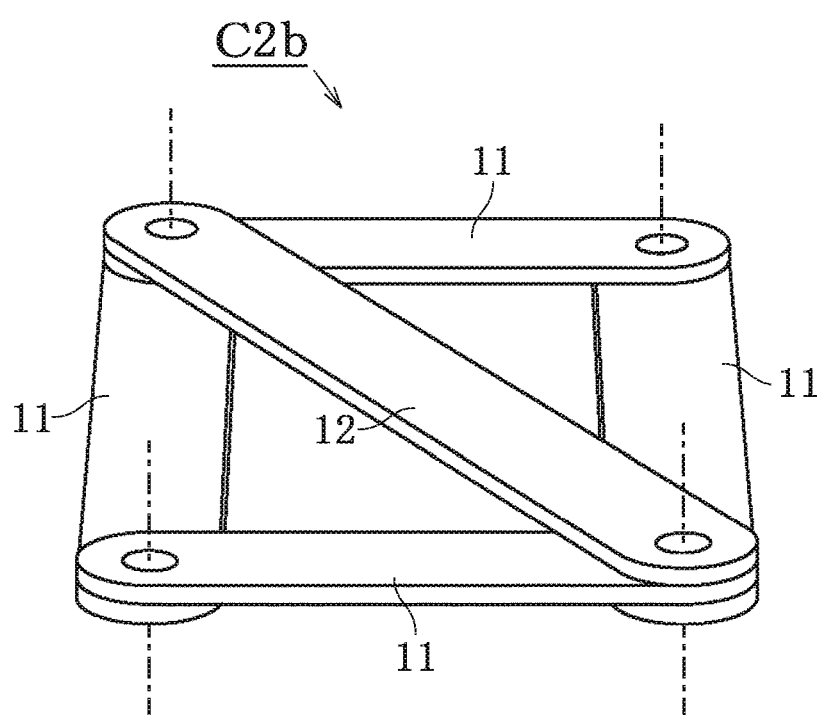
FIG. 16 is a perspective view illustrating an example where the couplers C2 illustrated in FIG. 15 have a function for fixing a distance between the probes.

Further, in correspondence to Example 3, a coupler C2b illustrated in FIG. 16 may be used to maintain a certain in-plane distance between the four probes PR13 to PR16 that are coupled together, whereby operational effects similar to those of Example 3 can be obtained.

The coupler C2b, as illustrated in FIG. 16, has a structure in which four I-shaped plate-like structures 11 of thermoplastic resin are joined together into a square shape, with a plate-like structure 12 further joined to form a diagonal of the square.

As described above, the probe holder 10 according to the second embodiment of the present invention is also configured such that, similarly to the probe holder 1 according to the first embodiment, a plurality of basic units 12 can be linked and fixed by the coupler C2 defining mutual angles and distances. Accordingly, it is possible, using a simple configuration, to adjust the arrangement of the probes PR11 to PR16 and to integrally increase the rigidity of the probes PR11 to PR16 and the probe holder 10, while ensuring a certain strictness with respect to any curved surface the head of the subject may have. In this way, it is possible to achieve highly stable holding of the probes PR11 to PR16 on the head of the subject.

REFERENCE SIGNS LIST 1, 1a, 1b, 1c, 1d, 1e, 1f, 1g, 10 Probe holder
2, 2a, 12 Basic unit
3 Rigid plate
3a Planar plate
C1, C2, C1a, C1b, C2b Coupler
PR1 to PR5, PR7, PR11 to PR16 Probe

The invention claimed is:

1. A probe holder to hold probes for emitting or detecting light and configured to attach the probes to the head of a subject, the probe holder comprising:
   a plurality of basic units each including a single plate that holds three of the probes, wherein the single plate has a triangle shape and each one of the three of the probes is disposed at a respective vertex of the triangle shape; and a plurality of couplers each linking adjacent three or more basic units of the plurality of basic units, wherein each of the plurality of couplers links a respective one of the three of the probes and adjacent probes to form a plurality of adjacent probes that are linked at a point equidistant from the plurality of adjacent probes, each probe in the plurality of adjacent probes being included in a different one of the plurality of basic units.

2. The probe holder according to claim 1, wherein the plurality of adjacent probes comprises three or four probes each included in the different one of the plurality of basic units.

3. The probe holder according to claim 1, wherein the single plate comprises a rigid plate having a predetermined curvature.

4. The probe holder according to claim 1, wherein the single plate comprises a planar plate.

5. The probe holder according to claim 1, wherein each of the plurality of couplers adjusts a lateral angle of the plurality of adjacent probes while maintaining an in-plane angle therebetween.

6. The probe holder according to claim 1, wherein each of the plurality of couplers is made of a thermoplastic resin, and maintains a constant in-plane angle between the plurality of adjacent probes.

7. The probe holder according to claim 5, wherein each of the plurality of couplers is joined to a respective plurality of adjacent probes.

8. The probe holder according to claim 5, wherein each of the plurality of couplers is joined to plates holding the plurality of adjacent probes.

9. The probe holder according to claim 1, wherein each of the plurality of couplers maintains a constant in-plane distance between the plurality of adjacent probes.

10. The probe holder according to claim 6, wherein each of the plurality of couplers is joined to the plurality of adjacent probes.

11. The probe holder according to claim 6, wherein each of the plurality of couplers is joined to plates holding the plurality of adjacent probes.

* * * * *